(12) United States Patent
Zhou

(10) Patent No.: US 9,894,931 B2
(45) Date of Patent: Feb. 20, 2018

(54) ANION ELECTRONIC CIGARETTE

(75) Inventor: Xuewu Zhou, Shenzhen (CN)

(73) Assignee: SHENZHEN BAUWAY TECHNOLOGY LIMITED, Shenzhen (CN)

( * ) Notice: Subject to any disclaimer, the term of this patent is extended or adjusted under 35 U.S.C. 154(b) by 923 days.

(21) Appl. No.: 13/985,700

(22) PCT Filed: Mar. 27, 2012

(86) PCT No.: PCT/CN2012/073089
§ 371 (c)(1),
(2), (4) Date: Sep. 19, 2014

(87) PCT Pub. No.: WO2013/075439
PCT Pub. Date: May 30, 2013

(65) Prior Publication Data
US 2015/0034104 A1    Feb. 5, 2015

(30) Foreign Application Priority Data

Nov. 25, 2011 (CN) .................. 2011 2 0476199 U

(51) Int. Cl.
*A24F 47/00* (2006.01)
*A61M 15/02* (2006.01)
(Continued)

(52) U.S. Cl.
CPC .......... *A24F 47/008* (2013.01); *A61M 15/02* (2013.01); *A61M 15/06* (2013.01); *H05B 3/03* (2013.01);
(Continued)

(58) Field of Classification Search
CPC ...... A24F 47/008; A61M 15/02; A61M 15/06
(Continued)

(56) References Cited

U.S. PATENT DOCUMENTS 5,574,619 A * 11/1996 Jeong .................. H01T 23/00
361/213
5,654,866 A * 8/1997 Jeong .................. A61L 9/22
348/E5.128

(Continued)

FOREIGN PATENT DOCUMENTS

CN         201188868 Y        3/2009
CN         201436037 U        4/2010
(Continued)

OTHER PUBLICATIONS

International Search Report for PCT/CN2012/073089.

*Primary Examiner* — Alexander Gilman
(74) *Attorney, Agent, or Firm* — JCIPRNET

(57) ABSTRACT

Provided is an anion electronic cigarette that includes an atomizer (1) and battery assembly (2) which are electrically connected to each other. The anionic electronic cigarette further includes an anion generation device, comprising an anion generator (14) which is electrically connected to the control circuit provided in the battery assembly (2). The anion electronic cigarette causes electronic smoke comprised of high-density anions to enter the human body, which can help smokers to mitigate the smoking addiction and even quit smoking, while providing a cleaner a method of smoking. At the same time, when it is required to add liquid tobacco tar into the electronic cigarette in the present invention, it only requires opening the cigarette nozzle and pulling out the sealing pillar from the tar injection hole to inject tobacco tar into the tobacco tar cavity, which is fast and convenient and is not easy for tar to leak.

8 Claims, 5 Drawing Sheets

(51) Int. Cl.
  *A61M 15/06*    (2006.01)
  *H05B 3/03*     (2006.01)
  *A61N 1/44*     (2006.01)

(52) U.S. Cl.
  CPC ........ *A61M 2205/8206* (2013.01); *A61N 1/44* (2013.01)

(58) Field of Classification Search
  USPC .......................................................... 131/329
  See application file for complete search history.

(56) References Cited

U.S. PATENT DOCUMENTS

| | | | | |
|---|---|---|---|---|
| 5,666,977 A * | 9/1997 | Higgins | ................ | A24F 47/008 128/200.14 |
| 8,833,364 B2 * | 9/2014 | Buchberger | ......... | A61M 11/041 128/200.14 |
| 2004/0047772 A1 * | 3/2004 | Kwak | ...................... | A61L 9/18 422/121 |
| 2006/0078460 A1 * | 4/2006 | Ryu | .......................... | A61L 9/12 422/5 |
| 2009/0095311 A1 * | 4/2009 | Han | ...................... | A24F 47/008 131/194 |
| 2010/0200008 A1 * | 8/2010 | Taieb | .................... | A24F 47/008 131/360 |
| 2010/0307518 A1 * | 12/2010 | Wang | .................... | A24F 47/008 131/329 |
| 2011/0277780 A1 * | 11/2011 | Terry | .................... | A24F 47/008 131/273 |
| 2012/0279512 A1 * | 11/2012 | Hon | ...................... | A24F 47/008 131/329 |
| 2013/0192618 A1 * | 8/2013 | Li | ......................... | A24F 47/008 131/329 |
| 2013/0319438 A1 * | 12/2013 | Liu | ....................... | A24F 47/008 131/329 |
| 2013/0333711 A1 * | 12/2013 | Liu | ....................... | A24F 47/008 131/329 |
| 2014/0190501 A1 * | 7/2014 | Liu | ....................... | A24F 47/008 131/329 |
| 2014/0311503 A1 * | 10/2014 | Liu | ........................ | G02B 27/18 131/329 |
| 2015/0020826 A1 * | 1/2015 | Liu | ....................... | A24F 47/008 131/329 |
| 2015/0034104 A1 * | 2/2015 | Zhou | ..................... | A24F 47/008 131/329 |
| 2015/0266032 A1 * | 9/2015 | Zhou | ..................... | B03C 3/0175 96/53 |
| 2015/0305410 A1 * | 10/2015 | Liu | ....................... | A24F 47/008 131/329 |
| 2016/0095357 A1 * | 4/2016 | Burton | .................. | A24F 47/008 131/328 |
| 2016/0128385 A1 * | 5/2016 | Lin | ....................... | A24F 47/002 131/328 |
| 2016/0150827 A1 * | 6/2016 | Liu | ....................... | A24F 47/008 131/329 |
| 2016/0192708 A1 * | 7/2016 | DeMeritt | ................. | H05B 3/40 131/329 |
| 2016/0192709 A1 * | 7/2016 | Liu | .......................... | H05B 3/40 131/329 |
| 2017/0196272 A1 * | 7/2017 | Li | ......................... | A24F 47/008 |

FOREIGN PATENT DOCUMENTS

| | | |
|---|---|---|
| JP | 2007-259840 A | 10/2007 |
| WO | WO2006/021153 A1 | 3/2006 |

\* cited by examiner

ANION ELECTRONIC CIGARETTE

CROSS REFERENCE TO RELATED APPLICATIONS

This application claims priority to patent applications: 1.) Patent Cooperation Treaty Application PCT/CN2012/073089, filed Mar. 26, 2012 and 2.) Chinese Patent Application CN201120476199.7, filed Nov. 25, 2011. Each of the above cited applications is hereby incorporated by reference herein as if fully set forth in its entirety.

TECHNICAL FIELD

The invention relates to an electronic cigarette, more particularly to An anion electronic cigarette capable of generating a large number of anions and convenient for the addition of tobacco tar.

BACKGROUND

At present, it is well known that electronic cigarette consists of an atomizer and a battery assembly, the atomizer consists mainly of an atomizing chamber, a tobacco tar storage cup, a sealing cover, a steel tube shell and a holder, however, when liquid tobacco tar is added to the electronic cigarette having such a structure, the shell must be removed at first, and then the tobacco tar storage cup is taken off for adding the liquid tobacco tar, this way is extremely complex and liable to cause tobacco tar leakage, hence, its use is quite inconvenient.

Moreover, most of people who smoke electronic cigarettes smoked general cigarettes in the past, vast harmful substances have been deposited in their body, electronic cigarettes could not help these people quit smoking even if they are capable of replacing common cigarettes temporarily, as a result, further improvement on the function of electronic cigarettes is required.

SUMMARY OF THE INVENTION

In view of the defects in the prior art, the invention provides An anion electronic cigarette, the electronic cigarette is provided with an anion generator therein, so a large number of anions are inhaled by people who smoke the electronic cigarette, thus contributing to the removal of harmful substances in human body and assisting smoker in resisting smoke temptation and even quitting smoking. Meanwhile, the improvement on the structure of the atomizer leads to more convenient addition of tobacco tar and low possibility of tobacco tar leakage.

In order to achieve the above objective, the invention adopts the technical proposal as follows:

An anion electronic cigarette comprises an atomizer and a battery assembly that are electrically connected with each other, and further comprises an anion generation device that comprises an anion generator and a control circuit, the anion generator is arranged on an electronic smoke flow channel and is electrically connected with the control circuit arranged inside the battery assembly.

Wherein, the atomizer comprises:

an ergonomic holder, the holder is internally provided with a hollow cavity, a smoke guide sleeve is fixed in the hollow cavity in the holder, and the smoke guide sleeve is provided with sealing cylinders (41) extending downwards;

an upper sealing ring, the upper sealing ring is provided with an axial through hole, the upper plate surface of the upper sealing ring is provided with an annular protrusion which is coaxial with the through hole, the annular protrusion is in coaxial airtight fit with the lower end of the through hole of the smoke guide sleeve, injection holes are arranged on the outside plate surface of the annular protrusion, the injection holes are in fluid-tight fit with the sealing cylinders; and the side surface of the sealing ring is provided with a sealing gasket;

a smoke generation device, the smoke generation device consists of an atomizing cover, a tobacco tar guide rope, a heating wire and an atomizing cup, an integrated smoke guide tube is arranged on the upper end of the atomizing cover and is internally communicated with the cover, the atomizing cover is respectively provided with a groove at the two sides in the diameter direction; an annular protrusion is arranged on the middle-upper part of the atomizing cup, the wall of the atomizing cup is respectively provided, in the diameter direction, with grooves capable of holding the tobacco tar guide rope, the atomizing cup is sleeved, above the annular protrusion, into the atomizing cover to form an atomizing hollow cavity, the groove is corresponding to the groove in position, the tobacco tar guide rope passes through the heating wire and then is arranged in the groove and the end tip of the rope extends out of the atomizing hollow cavity; and the heating wire is electrically connected with the battery assembly (2);

a lower sealing ring, the sealing ring is provided with a through hole in fluid-tight fit with the lower end of the atomizing cup, a groove in fit with the annular protrusion of the atomizing cup is arranged on the upper end face of the sealing ring, and a sealing gasket is arranged at the outer side of the lower sealing ring;

a smoke guide tube, one end of the smoke guide tube is connected with the lower end of the through hole of the upper sealing ring in an airtight fit manner, and the other end is connected with the smoke guide tube on the upper end of the atomizing cover in an airtight fit manner and supports the upper sealing ring and the atomizing cover;

an atomizer shell, the upper end of the straight barrel-shaped atomizer shell is in fit connection with the holder; the upper sealing ring, the smoke guide tube, the smoke generation device and the lower sealing ring are accommodated in the hollow cavity inside the shell to form an electronic cigarette atomizer, the upper sealing ring and the lower sealing ring form an electronic cigarette tobacco tar cavity together with the hollow cavity inside the shell, and smoke inlet holes are arranged on the side surfaces of the lower end of the atomizer shell.

The anion generator is arranged on a smoke channel on the bottom of the electronic cigarette atomizer, and a smoke flow passes through the anion generator before entering the atomizer, so as to generate a large number of anions.

An annular protrusion is arranged outwards on the lower end of the smoke guide sleeve, the two sealing cylinders extending downwards are respectively arranged on a diameter line of the annular protrusion, and the upper sealing ring is provided with the injection holes that are corresponding to the two sealing cylinders in position and are in fluid-tight fit with the two sealing cylinders.

A mounting portion is arranged on the lower end of the atomizer shell and is sleeved with a decorative ring, the decorative ring is provided with smoke through holes corresponding to the smoke inlet holes, and two mounting bayonets are arranged on the two sides of the mounting portion and are used for the connection with the battery assembly.

The atomizing cup is made of a ceramic material.

The heating wire is connected with an electrode contact plate via a lead wire, and the electrode contact plate is provided with electrode contacts.

The electronic cigarette has a flat section.

The electronic cigarette further comprises a holder cover in fit with the holder.

Since the structure above is adopted, the anion generator is arranged in the electronic cigarette of the invention, high-concentration anions enter into human body through electronic smoke when people smoke the electronic cigarette, thus contributing to the removal of harmful substances in human body and assisting smoker in resisting smoke temptation and even quitting smoking. Meanwhile, when the addition of liquid tobacco tar is required, only the holder of the electronic cigarette of the invention needs to be opened and the sealing cylinders are pulled out of the injection holes so as to inject the tobacco tar into the tobacco tar cavity, which is convenient, fast, and difficult to cause tobacco tar leakage.

DETAILED DESCRIPTION OF THE EMBODIMENTS

Detailed Description is made below to the invention with reference to the drawings and the embodiments.

Figure 1:
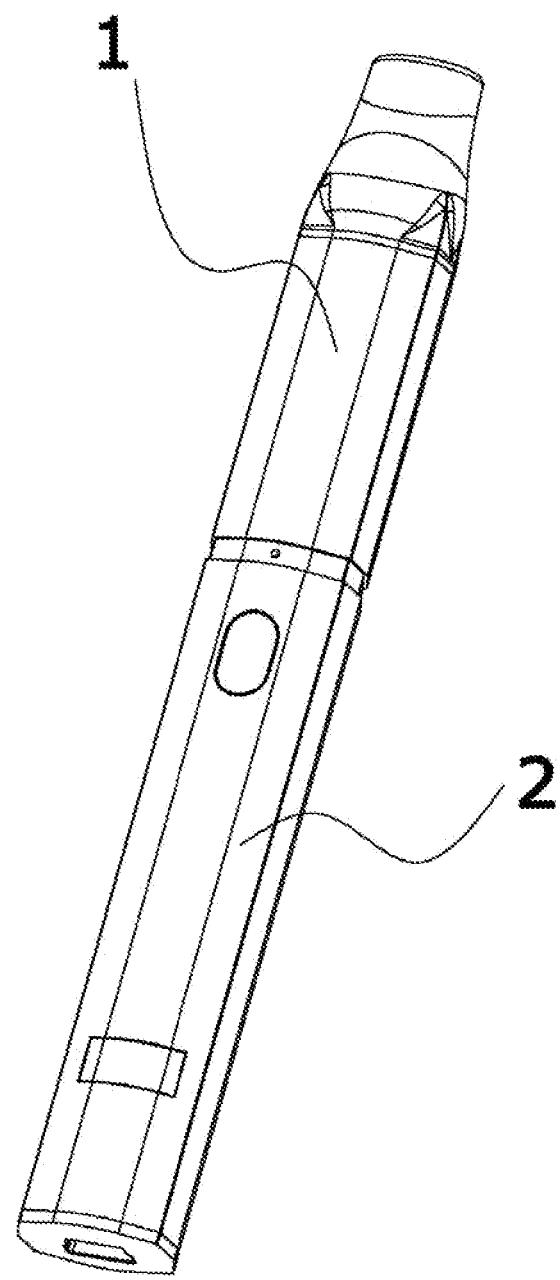
FIG. 1 is a structural schematic diagram of the invention.
Figure 2:
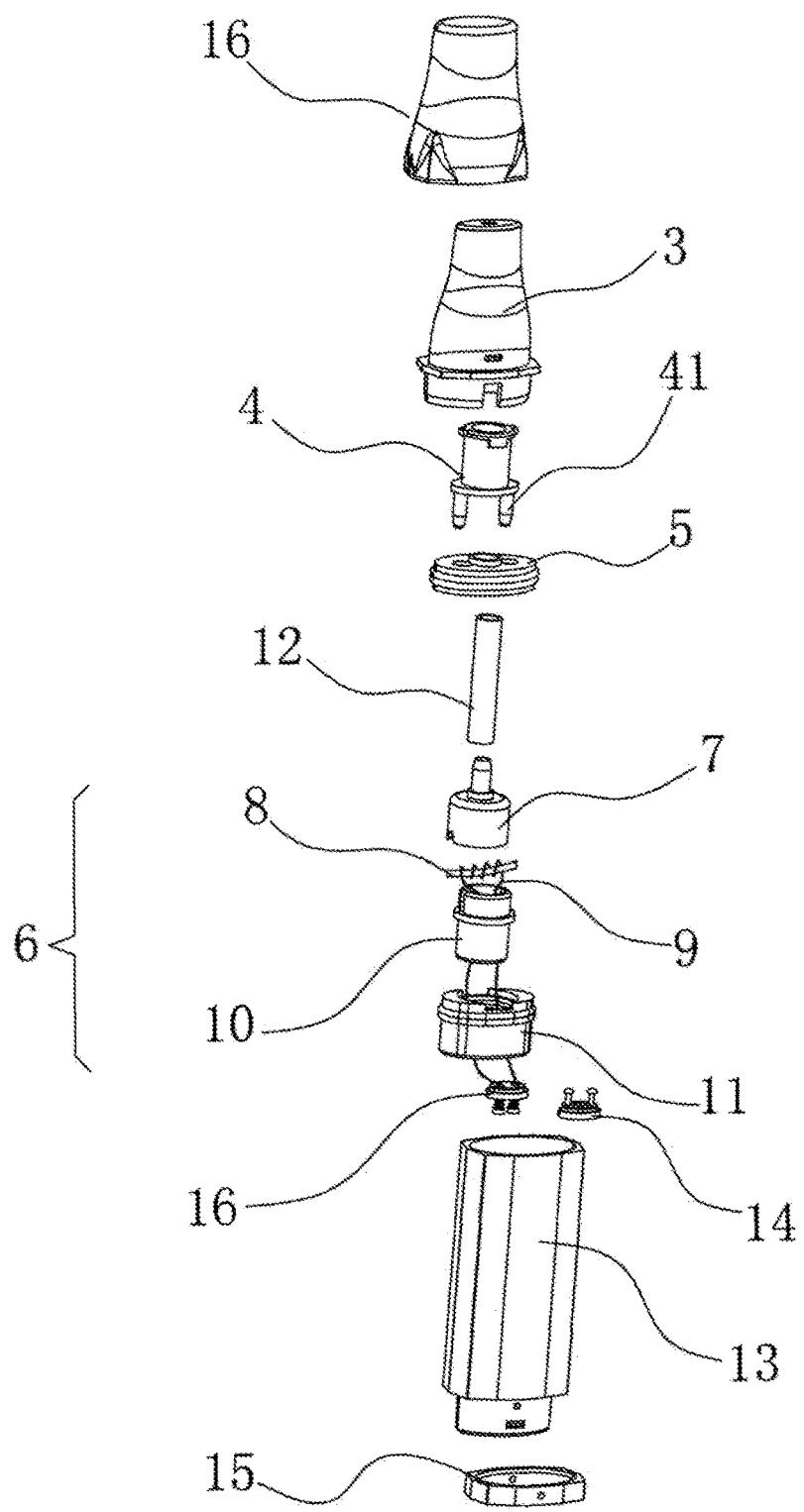
FIG. 2 is an exploded view of the smoke guide sleeve of FIG. 1.

Referring to FIG. 1 and FIG. 2, a negative electronic cigarette of the invention having a flat section comprises an atomizer 1 and a battery assembly 2 that are electrically connected with each other. Meanwhile, the anion electronic cigarette further comprises an anion generation device that comprises an anion generator 14 and a control circuit (not shown in the drawings), the anion generator 14 is arranged on an electronic smoke flow channel and is electrically connected with the control circuit arranged inside the battery assembly 2.

Wherein, the atomizer comprises an ergonomic holder 3, an upper sealing ring 5, a smoke guide tube 12, a smoke generation device 6, a lower sealing ring 11 and an atomizer shell 13.

Figure 3:
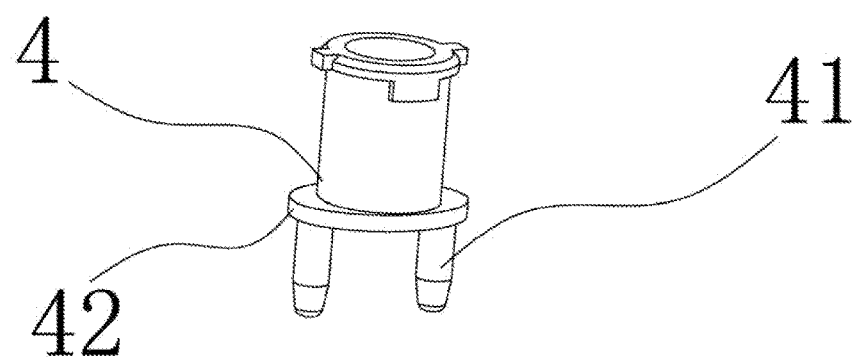
FIG. 3 is an enlarged view of the smoke guide sleeve of the invention.

The atomizer shell 13 is internally provided with a hollow cavity, a smoke guide sleeve 4 is fixed in the hollow cavity in the holder 3, an annular protrusion 42 is arranged outwards on the lower end of the smoke guide sleeve 4, and two sealing cylinders 41 extending downwards are respectively arranged on a diameter line of the annular protrusion 42. (Referring to FIG. 3)

Figure 4:
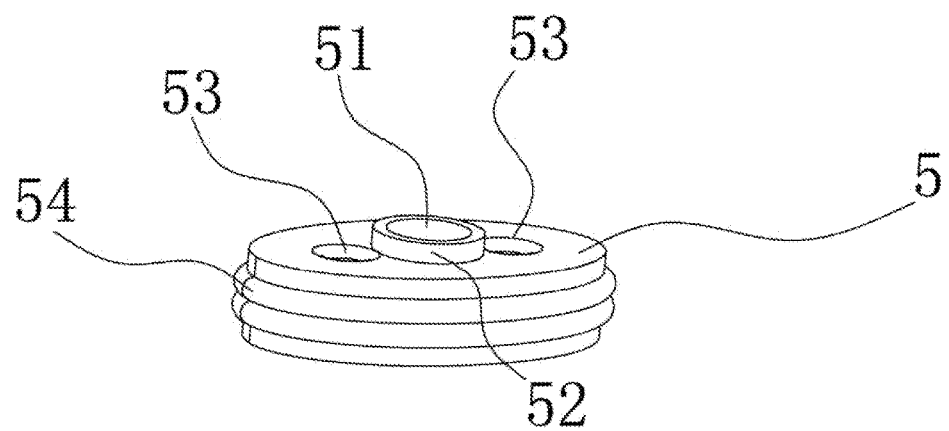
FIG. 4 is an enlarged view of the upper sealing ring of the invention.

The upper sealing ring 5 is provided with an axial through hole 5, the upper plate surface of the upper sealing ring 5 is provided with an annular protrusion 52 which is coaxial with the through hole 51, the annular protrusion 52 is in coaxial airtight fit with the lower end of the through hole of the smoke guide sleeve 4, two injection holes 53 are arranged on the outside plate surface of the annular protrusion 52, the injection holes 53 are in fluid-tight fit with the sealing cylinders 41; and the side surface of the sealing ring 5 is provided with a sealing gasket 54. (Referring to FIG. 4)

Figure 5:
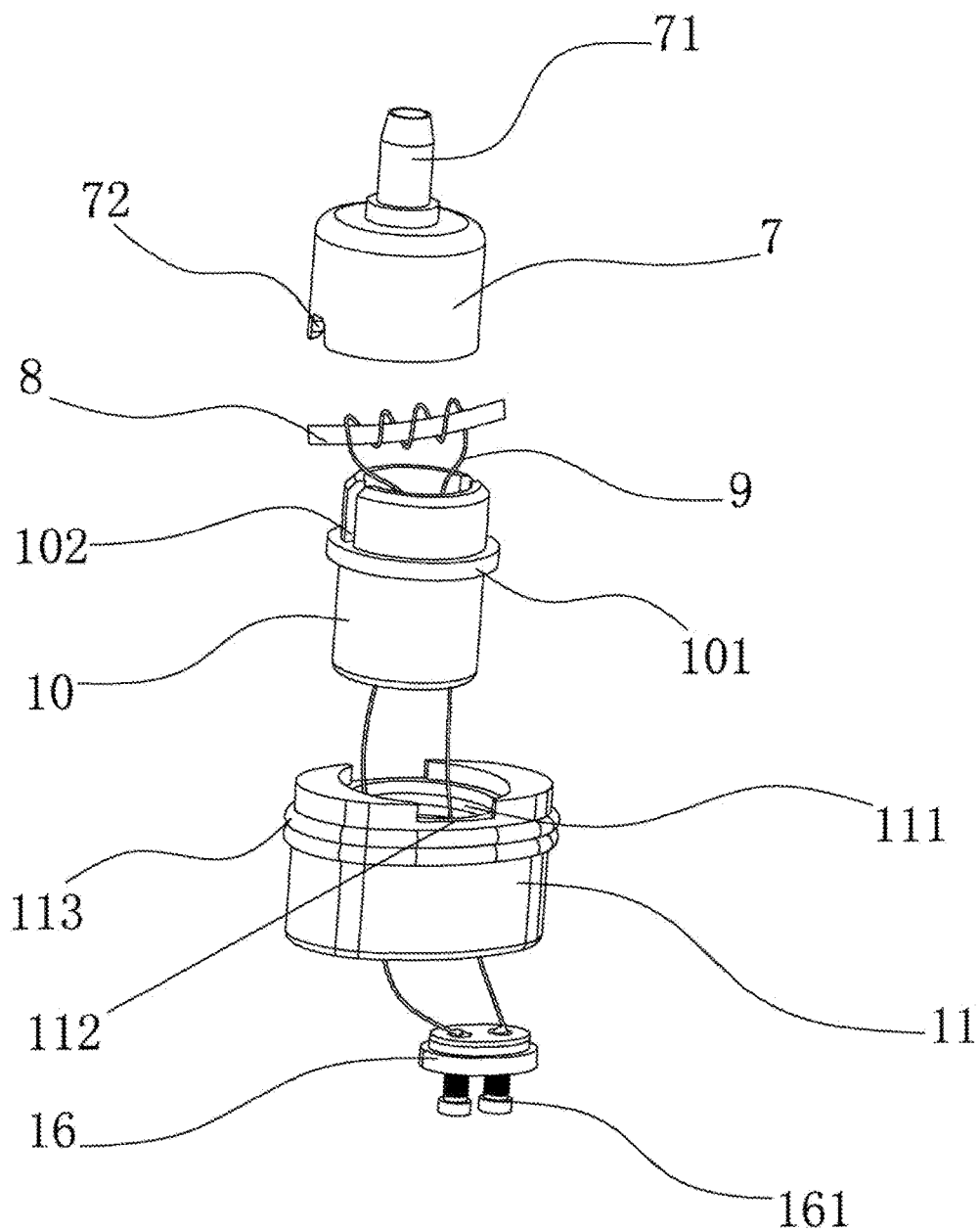
FIG. 5 is an enlarged view of the smoke generation device and the lower sealing ring of the invention.
Figure 6:
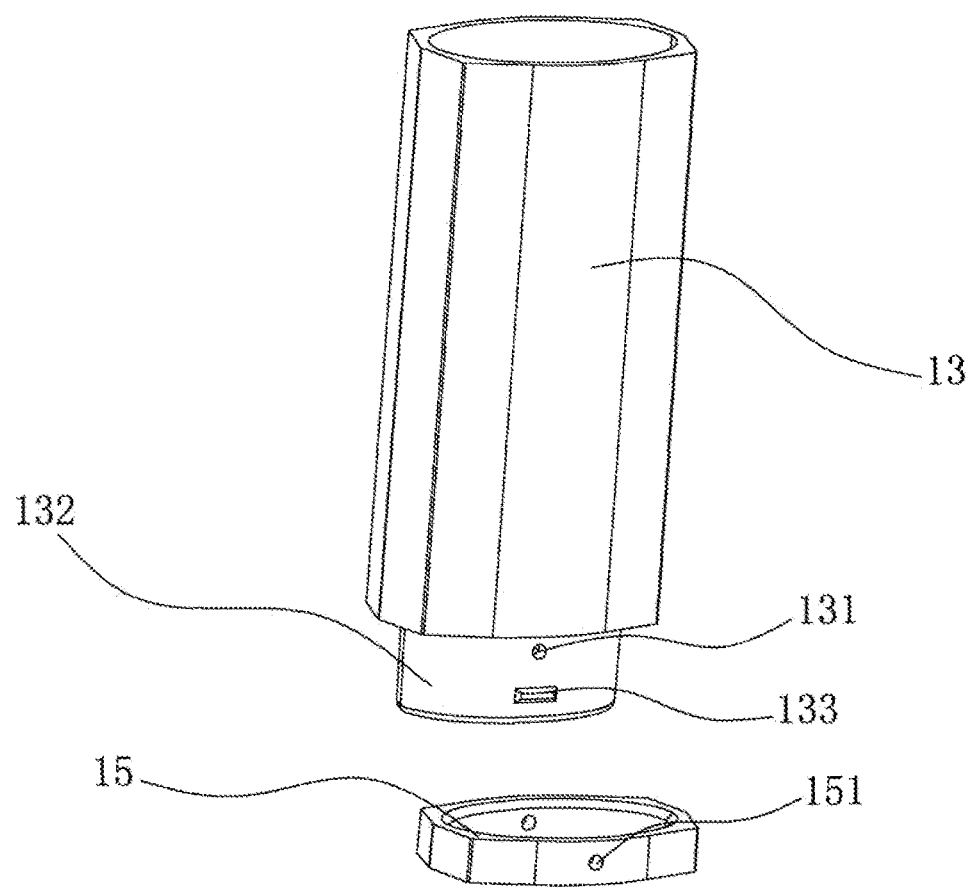
FIG. 6 is an enlarged view of the atomizer shell of the invention.

The smoke generation device 6 consists of an atomizing cover 7, a tobacco tar guide rope 8, a heating wire 9 and an atomizing cup 10, an integrated smoke guide tube 71 is arranged on the upper end of the atomizing cover 7 and is internally communicated with the cover, the atomizing cover 7 is respectively provided with a groove 72 at the two sides in the diameter direction. An annular protrusion 101 is arranged on the middle-upper part of the atomizing cup 10 which is made of a ceramic material, the wall of the atomizing cup 10 is respectively provided, in the diameter direction, with grooves 102 capable of holding the tobacco tar guide rope 8, the atomizing cup 10 is sleeved, above the annular protrusion 101, into the atomizing cover 7 to form an atomizing hollow cavity, the groove 72 is corresponding to the groove 102 in position. The tobacco tar guide rope 8 passes through the heating wire 9 and then is arranged in the groove 102 and the end tip of the rope extends out of the atomizing hollow cavity. The heating wire 9 is connected with an electrode contact plate 16 via a lead wire, the electrode contact plate is provided with electrode contacts 161, and the electrode contacts 161 are electrically connected with the battery assembly 2. (Referring to FIG. 5)

The lower sealing ring 11 is provided with a through hole 111 in fluid-tight fit with the lower end of the atomizing cup 10, a groove 112 in fit with the annular protrusion 101 of the atomizing cup 10 is arranged on the upper end face of the sealing ring, and a sealing gasket 113 is arranged at the outer side of the lower sealing ring 11. (Referring to FIG. 5)

One end of the smoke guide tube 12 is connected with the lower end of the through hole 51 of the upper sealing ring 5 in an airtight fit manner, and the other end is connected with the smoke guide tube 71 on the upper end of the atomizing cover 7 in an airtight fit manner and supports the upper sealing ring 5 and the atomizing cover 7.

The upper end of the straight barrel-shaped atomizer shell 13 is in fit connection with the holder 3; the upper sealing ring 5, the smoke guide tube 12, the smoke generation device 6 and the lower sealing ring 11 are accommodated in the hollow cavity inside the shell to form an electronic cigarette atomizer, and the upper sealing ring 5 and the lower sealing ring 11 form an electronic cigarette tobacco tar cavity together with the hollow cavity inside the shell. A mounting portion 132 is arranged on the lower end of the atomizer shell 13, the mounting portion 132 is provided with two smoke inlet holes 131 and is sleeved with a decorative ring 15, the decorative ring 15 is provided with smoke through holes 151 corresponding to the smoke inlet holes 131, and two mounting bayonets 133 are arranged on the two sides of the mounting portion and are used for the clamped connection with the battery assembly.

The embodiments discussed above are merely for describing the invention better and are not intended to limit the scope of the invention, therefore, slight changes and equivalent variations made without departing from the spirit of this patent shall be contemplated as being within the scope of the invention.

The invention claimed is:

1. An anion electronic cigarette, comprising an atomizer (1) and a battery assembly (2) that are electrically connected with each other, characterized in that: the anion electronic cigarette further comprises an anion generation device that comprises an anion generator (14) and a control circuit, the generator (14) is arranged on an electronic smoke flow channel, wherein the atomizer (1) comprises:

an ergonomic holder (3), the holder (3) being internally provided with a hollow cavity, a smoke guide sleeve (4) being fixed in the hollow cavity in the holder (3), and the smoke guide sleeve (4) being provided with sealing cylinders (41) extending downwards;

an upper sealing ring (5), the upper sealing ring (5) being provided with an axial through hole (51), the upper plate surface of the upper sealing ring (5) being provided with an annular protrusion (52) which is coaxial with the though hole (51), the annular protrusion (52) being in coaxial airtight fit with the lower end of the through hole of the smoke guide sleeve (4), injection holes (53) being arranged on the outside plate surface of the annular protrusion (52), the injection holes (53) being in fluid-tight fit with the sealing cylinders (41); and the side surface of the sealing ring (5) being provided with a sealing gasket (54);

an smoke generation device (6), the smoke generation device (6) consisting of an atomizing cover (7), a tobacco tar guide rope (8), a heating wire (9) and an atomizing cup (10), an integrated smoke guide tube (71) being arranged on the upper end of the atomizing cover (7) and being internally communicated with the cover, the atomizing cover (7) being respectively provided with a groove (72) at the two sides in the diameter direction; and annular protrusion (101) being arranged on the middle-upper part of the atomizing cup (10), the wall of the atomizing cup (10) being respectively provided, in the diameter direction, with groves (102) capable of holding the tobacco tar guide rope (8), the atomizing cup (10) being sleeved, above the annular protrusion (101), into the atomizing cover (7) to form an atomizing hollow cavity, the groove (72) being corresponding to the groove (102) in position, the tobacco tar guide rope (8) passing through the heating wire (9) and then being arranged in the groove (102) and the end tip of the rope extending out of the atomizing hollow cavity; and the heating wire (9) being electrically connected with the battery assembly (2);

a lower sealing ring (11), the sealing ring (11) being provided with a through hole (111) in fluid-tight fit with the lower end of the atomizing cup (10, a groove (112) in fit with the annular protrusion (101) of the atomizing cup (10) being arranged on the upper end face of the sealing ring, and a sealing gasket (113) being arranged at the outer side of the lower sealing ring (11);

a smoke guide tube (12), one end of the smoke guide tube (12) being connected with the lower end of the through hole (51) of the upper sealing ring (5) in an airtight fit manner, and the other end being connected with the smoke guide tube (71) on the upper end of the atomizing cover (7) in an airtight fit manner and supporting the upper sealing ring (5) and the atomizing cover (7);

an atomizer shell (13), the upper end of the straight barrel-shaped atomizer shell (13) being in fit connection with the holder (3); the upper sealing ring (5), the smoke guide tube (12), the smoke generation device (6) and the lower sealing ring (11) being accommodated in the hollow cavity inside the shell to form an electronic cigarette tobacco tar cavity together with the hollow cavity inside the shell, and smoke inlet holes (131) being arranged on the side surfaces of the lower end of the atomizer shell (13).

2. The anion electronic cigarette according to claim 1, characterized in that the anion generator (14) is arranged on a smoke channel on the bottom of the electronic cigarette atomizer, and a smoke flow passes through the anion generator (14) before entering the atomizer, so as to generate a large number of anions.

3. The anion electronic cigarette according to claim 1, characterized in that an annular protrusion (42) is arranged outwards on the lower end of the smoke guide sleeve (4), the two sealing cylinders (41) extending downwards are respectively arranged on a diameter line of the annular protrusion (42), and the upper sealing ring (5) is provided with the injection holes (53) that are corresponding to the two sealing cylinders (41) in position and are in fluid-tight fit with the two sealing cylinders (41).

4. The anion electronic cigarette according to claim 1, characterized in that a mounting portion (132) in arranged on the lower end of the atomizer shell (13) and is sleeved with a decorative ring (15), the decorative ring (15) is provided with smoke through holes (151) corresponding to the smoke inlet holes (131), and two mounting bayonets (133) are arranged on the two sides of the mounting portion and are used for the connection with the battery assembly (2).

5. The anion electronic cigarette according to claim 1, characterized in that the atomizing cup (10) is made of a ceramic material.

6. The anion electronic cigarette according to claim 1, characterized in that the heating wire (9) is connected with an electrode contact plate (16) via a lead wire, and the electrode contact plate is provided with electrode contacts (161).

7. The anion electronic cigarette according to claim 1, characterized in that the electronic cigarette has a flat section.

8. The anion electronic cigarette according to claim 1, characterized in that the electronic cigarette further comprises a holder cover in fit with the holder.

* * * * *